United States Patent
Jacobsen et al.

(10) Patent No.: US 6,260,458 B1
(45) Date of Patent: Jul. 17, 2001

(54) METHOD AND APPARATUS FOR FORMING CUTS IN CATHETERS, GUIDE WIRES, AND THE LIKE

(75) Inventors: Stephen C. Jacobsen; Clark Davis, both of Salt Lake City, UT (US)

(73) Assignee: Sarcos L.C., Salt Lake City, UT (US)

( * ) Notice: Subject to any disclaimer, the term of this patent is extended or adjusted under 35 U.S.C. 154(b) by 0 days.

(21) Appl. No.: 09/366,360

(22) Filed: Aug. 3, 1999

Related U.S. Application Data

(62) Division of application No. 08/714,555, filed on Sep. 16, 1996, now Pat. No. 6,014,919.

(51) Int. Cl.[7] .............................. B26D 5/02; B26D 5/20; B26D 7/02
(52) U.S. Cl. .............................. 83/227; 83/886; 83/210; 83/248; 83/282; 83/421; 83/422; 83/465; 83/471.2; 83/486; 83/733
(58) Field of Search .............................. 83/209, 210, 240, 83/248, 257, 282, 409, 418, 421, 457, 465, 466.1, 471.2, 471.3, 485, 486, 486.1, 556, 563, 733, 863, 864, 881, 886, 913, 924, 950, 422, 227; 269/254 R, 902; 279/46.1

(56) References Cited

U.S. PATENT DOCUMENTS

| | | |
|---|---|---|
| 1,553,227 | 9/1925 | Feyk et al. .............................. 83/409 |
| 1,866,888 | 7/1932 | Hawley .............................. 83/471.3 |
| 3,686,990 | 8/1972 | Margolien .............................. 83/409 |
| 4,000,672 | 1/1977 | Sitterer et al. ...................... 83/209 X |
| 4,476,754 | 10/1984 | Ducret .............................. 83/210 X |
| 4,574,670 | 3/1986 | Johnson .............................. 83/409 |
| 4,781,092 | 11/1988 | Gaiser .............................. 83/282 X |
| 4,922,777 | 5/1990 | Kawabata .............................. 83/409 X |
| 5,009,137 | 4/1991 | Dannatt .............................. 83/209 |
| 5,308,435 | 5/1994 | Ruggles et al. ...................... 83/209 X |
| 5,315,906 | 5/1994 | Ferenczi et al. .................... 83/282 X |
| 5,460,187 | 10/1995 | Daigle et al. . |

FOREIGN PATENT DOCUMENTS

WO 93/04722   3/1993   (WO) .

*Primary Examiner*—Charles Goodman
(74) *Attorney, Agent, or Firm*—Thorpe North & Western

(57) ABSTRACT

A system and method for making at least one cut in a catheter, guide wire or other elongate cylindrical object having a lengthwise axis, comprising a securing means for repeatedly releasing and then holding the elongate object in a position suitable for cutting it at an angle or transversely relative to its lengthwise axis, a manipulating means for moving the elongate object so that it can be disposed in the position suitable for cutting when it is released by the securing means, and a cutting means for forming the at least one precision cut in the elongate object to any desired depth. The securing means preferably comprises a rotatable collet clamp, and the manipulating means preferably comprises a pinch roller assembly for advancing and holding the elongate object. The cutting means is preferably a mechanical blade mounted on a rotatable spindle, and is free to move vertically and horizontally with respect to the elongate object to thereby control the location, size and depth of the cuts in the cylindrical object disposed adjacent thereto. The clamp is configured to hold and position the object to be cut so as to expose the entire circumference of the cylindrical object to the saw blade if desired. By releasing the clamp, the pinch roller advances the cylindrical object before the clamp is re-engaged to securely hold the cylindrical object for cutting.

15 Claims, 4 Drawing Sheets

METHOD AND APPARATUS FOR FORMING CUTS IN CATHETERS, GUIDE WIRES, AND THE LIKE

This application is a division of U.S. patent application Ser. No. 08/714,555, filed on Sep. 16, 1996 now U.S. Pat. No. 6,014,919.

BACKGROUND

1. Field of the Invention

The present invention pertains to making precision cuts in catheters and guide wires. Specifically, a device for holding, advancing, rotating and then cutting a catheter or guide wire is provided which is able to manipulate the catheter or guide wire in two degrees of freedom to enable precision control of the location of the cuts. Various clamping mechanisms are provided for manipulating the catheter or guide wire, resulting in controlled variation in mechanical properties.

2. State of the Art

Making cuts in catheters and guide wires requires precision in order to ensure reliability because of the medical applications in which they are used. However, it is also important to control costs of production so that costs to the health care industry can be minimized.

The state of the art is typified by such devices as grinding wires, wound coils, and lasers for making the cuts. But these devices often suffer from high cost or imprecise or difficult control mechanisms for properly positioning both the device to make the cut and the cylindrical object to be cut.

What is needed is a method and apparatus for making cuts in catheters and guide wires which allows precise control of characteristics of the cuts. This entails precision holding, advancement and rotation of the generally cylindrical object while at least one saw blade is itself advanced to make the cut and retracted afterward.

OBJECTS AND SUMMARY OF THE INVENTION

It is therefore an object of the present invention to provide a method and apparatus for forming precision cuts in elongate cylindrical objects including catheters and catheter guide wires.

It is another object to provide a method and apparatus for forming precision cuts by manipulating a cylindrical object in two degrees of freedom to control the parameters of the cuts.

It is yet another object to provide a method and apparatus for holding, advancing and rotating a cylindrical object to be cut.

These and other objects are realized in a preferred embodiment of a system for making cuts in a catheter, guide wire or other elongate cylindrical object having a lengthwise axis. The system generally comprises a securing means for repeatedly releasing and then holding the elongate object in a position suitable for cutting it at an angle or transversely relative to its lengthwise axis, a manipulating means for moving the elongate object so that it can be disposed in the position suitable for cutting when it is released by the securing means, and a cutting means for forming the at least one precision cut in the elongate object to any desired depth. The securing means preferably comprises a rotatable collet clamp. The manipulating means preferably comprises a pinch roller assembly for advancing and holding the elongate object. The cutting means is preferably a mechanical blade mounted on a rotatable spindle. The clamp is able to hold the object to be cut, as well as position it by, for example, rotation to thereby expose the entire circumference of the cylindrical object to the saw blade. By releasing the clamp, the pinch roller advances the cylindrical object before the clamp is re-engaged to securely hold the cylindrical object for cutting.

The securing means, manipulating means, and cutting means are preferably mounted on a base. The rotating spindle is free to move vertically and horizontally with respect to the base to thereby control the location, length, depth and angle of the cuts in the cylindrical object disposed adjacent thereto.

Another aspect of the invention is the ability to make precision cuts by providing means for controlling the rotation and advancement of the object to be cut and movement of the saw blade spindle member.

Another aspect is the ability to simultaneously make a plurality of cuts in the object. This is accomplished with a saw blade having a plurality of blades in parallel. Even more cuts can be made by providing more than one saw blade spindle member, where each is independently movable in two degrees of freedom.

Another aspect of the invention is to provide more than one spindle member so that blades can simultaneously make precision cuts at different locations along the length of the cylindrical object.

These and other objects, features, advantages and alternative aspects of the present invention will become apparent to those skilled in the art from a consideration of the following detailed description taken in combination with the accompanying drawings.

DETAILED DESCRIPTION OF THE PREFERRED EMBODIMENT

Reference will now be made to the drawings in which the various elements of the present invention will be given numerical designations and in which the invention will be discussed so as to enable one skilled in the art to make and use the invention.

Figure 1A:
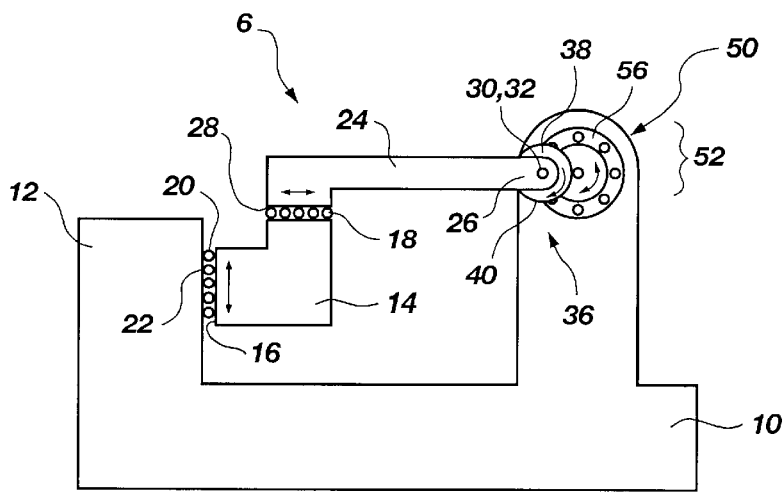
FIG. 1A is a front elevational view of a preferred embodiment made in accordance with the principles of the present invention.
Figure 1B:
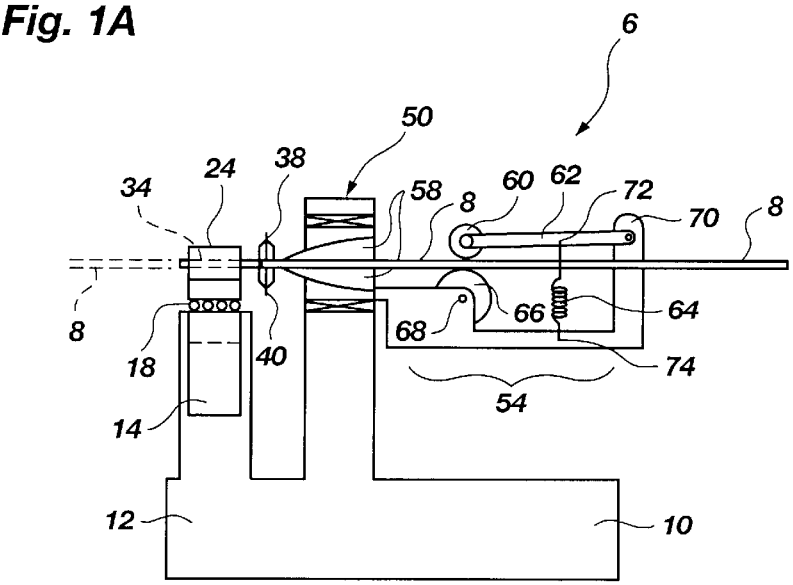
FIG. 1B is a side elevational view of the invention shown in FIG. 1A.

The present invention is illustrated in FIGS. 1A and 1B. FIG. 1A is a front view of the preferred embodiment of the invention, and shows the system for forming precision cuts in a catheter, a guide wire, or other cylindrical objects. For purposes of keeping in mind the intended use of the present invention, a catheter will be referred to as the object being cut, although any cylindrical object can be substituted for the catheter. However, reference to the catheter is only for the convenience of writing in terms of a specific cylindrical object, and should not be considered a material limitation of the invention. However, referring to a catheter keeps present in mind the objective of having a very precise cutting device, where precision is paramount in most medical applications. Furthermore, a catheter is only one embodiment of a medical application, but which easily represents the need for precision.

The system 6 shown in FIGS. 1A and 1B is comprised of several elements including a base member 10 for supporting the structure. Coupled in sliding engagement with a vertical base member 12 is a vertically movable member 14 which has a first vertical coupling face 16 and a first horizontal coupling face 18. The vertical coupling face 16 is slidingly engaged with a base member vertical coupling face 20.

The mechanism 22 for enabling the sliding engagement between the vertical coupling face 16 and the base member vertical coupling face 20 can be any appropriate apparatus. The important consideration is that the vertically movable member 14 not be permitted to move horizontally, or the precision of the system will be compromised. Therefore, the tolerances of the mechanism 22 must necessarily be small. A good example of an appropriate mechanism 22 is well known to those skilled in the art as a crossed roller bearing slide.

Figure 2:
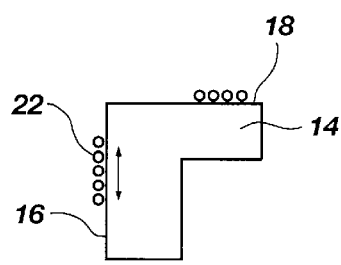
FIG. 2 is an alternative embodiment of a vertically moving member shown reversed in orientation with respect to FIGS. 1A and 1B.
Figure 3:
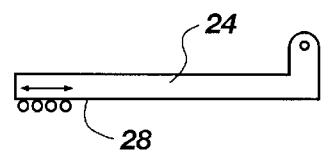
FIG. 3 is an alternative embodiment of a horizontally moving member shown reversed in orientation with respect to FIGS. 1A and 1B.

The shape of the vertically movable member 14 is shown here as a small backwards "L". An alternative shape for the vertically movable member 14 is shown in FIG. 2. The member 14 is flipped over as compared to the embodiment of FIG. 1A. The important feature of the member 14 is that it provide two faces 16, 18 which can be slidably engaged to move vertically and provide a second face on which another member can slidably engage to move horizontally.

The system in FIGS. 1A and 1B is also comprised of a horizontally movable member 24 which has a spindle end 26 and a second horizontal coupling face 28. This horizontally movable member 24 is slidably engaged at its second horizontal coupling face 28 to the vertically movable member 14 at its first horizontal coupling face 18. It should be observed that the vertically movable member 14 and the horizontally movable member 24 are capable of moving independently of each other. In this way, the system achieves two independent degrees of freedom of movement.

The spindle end 26 of the horizontally movable member 24 provides a horizontal slot 30 in which a spindle 32 is disposed.

The slot 30 is generally circular to serve as a receptor for the round shaft 34 of the spindle 32. The spindle shaft 34 has disposed on a working end 36 thereof at least one circular saw blade 38. The circular saw blade 38 is disposed vertically on the spindle shaft 34, but may also be angled in other embodiments.

The spindle shaft 34 is coupled to a drive motor by gears, belts, direct drive, or any other appropriate means (not shown) which will cause the spindle shaft 34 to rapidly rotate. The drive motor (not shown) can be disposed in any appropriate location relative to the spindle shaft. In a preferred embodiment, the spindle shaft 34 is driven by a brushless DC motor through a toothed timing belt.

The circular saw blade 38 is typical of those found in the art. In a preferred embodiment, the cutting edge 40 of the saw blade 38 is coated with industrial diamonds.

The means for holding and otherwise manipulating a catheter 8 to be cut is the clamping member 50. The clamping member 50 is comprised of two major assemblies: the clamp 52 and the clamp feeding (supplying) means 54, or the device which feeds the catheter 8 to and then through the clamp 52. The clamping member 50 is also coupled to the base member 10 and disposed to hold the clamp 52 in a position for easy feeding of the catheter 8 to the circular saw blade 38.

In the preferred embodiment, the clamp 52 is of the type known to those skilled in the art as a collet clamp. A collet clamp is a slotted cylindrical clamp inserted tightly into the tapered interior of a sleeve or chuck on a lathe to hold a cylindrical piece of work. In FIG. 1A, the cylindrical shape of the clamp 52 is visible. It is slotted in that the clamping arms 58 are separate from each other so that they can pull away from the catheter 8 when disengaging, and then securely come together around the catheter 8 when engaging.

In a preferred embodiment, a desirable feature of the clamp 52 is that it is rotatably mounted within the clamping member 50. The collet clamp 52 can then rotate so as to dispose a different portion of the surface of the catheter 8 to the saw blades 38. The mechanism for rotating the clamp 52 is shown generally at 56, and is comprised of the clamp 52 which is held in a frame which can rotate with respect to the saw blade 38.

The clamp feeding (supplying) means 54 seen in FIG. 1B is shown in this preferred embodiment to be comprised of a pinch roller assembly 60, 62 working in conjunction with a feed roller 66. As FIG. 1B should make clear, the pinch roller assembly 60, 62 feeds the catheter 8 to the clamp 52 by using friction created between two opposing members 60, 66. The upper member is the pinch roller 60. The lower member is the feed roller 66. The feed roller 66 has an axle 68 mounted in the clamp feeding means 54 so that the feed roller 66 can roll. The pinch roller 60 is disposed at the end of a lever arm 62 which pivots at a pivoting end 70. Located distally from the pinch roller assembly along the length of the lever arm is a hole 72. One end of a spring 64 is inserted therethrough, and the other end of the spring 64 is coupled at another hole 74 to the clamp feeding means 54. The spring 64 provides the tension necessary for the feed roller 64 to push the catheter 8 to the clamp 52.

Having described most of the components in a preferred embodiment of the catheter cutting assembly 6, the operation of the assembly 6 is as follows. First, the uncut catheter 8 is placed between the pinch roller 60 and the feed roller 66. This can be done by raising the lever arm 62 by stretching the spring 64. Releasing the lever arm 62 causes the pinch roller 60 to push down against the feed roller 66, with the catheter 8 disposed therebetween. A drive mechanism (not shown) is coupled to the feed roller 66 to cause it to roll and thereby push the catheter 8 toward the clamp 52. The clamp 52 should be in a disengaged position (hole through clamp is larger than diameter of the catheter 8) so that the catheter 8 can be fed easily therethrough. After passing through the clamp 52, the catheter 8 is fed sufficiently far past the circular saw blade 38 so that it is in a proper position to have an incision made in or through its surface.

When the catheter 8 is positioned correctly, the clamp 52 is engaged and the saw blade 38 is advanced to make cutting contact. Before cutting, the saw blade 38 will always be positioned in a retracted position. The retracted position is both vertically below and horizontally pulled away from the catheter 8. The first movement of the saw blade 38 is 1) horizontal advancement toward the catheter 8. This is accomplished by moving the horizontally movable member 24 relative to the vertically movable member 14 to which it is attached. The horizontally movable member 24 is moved until it has reached the depth of the incision to be made in the catheter 8. The next step 2) comprises the vertically movable member 14 moving upwards relative to the base 10 to which is coupled to thereby make the cut. The saw blade 38 is then immediately retracted by moving the vertically movable member 14 away from the catheter 8. The horizontal member is moved only when the next cut is at a different depth or when all cutting is complete.

If another cut is to be made, the collet clamp 52 is released as step 4). The catheter 8 is then fed through the clamp 52 by the feed roller 66 as step 5). The collet clamp 52 is then re-engaged in step 6) and, if necessary, the collet clamp 52 is rotated to expose a different position of the catheter 8 to the saw blade 38. The saw blade 38 is then moved horizontally if the depth of cut is to change, and then vertically to make the cut and steps 1) through 7) repeat as often as necessary until all the incisions have been made or the catheter 8 is no longer capable of being grasped by the feed roller 66 and opposing pinch roller 60.

The above description of the operation of the catheter cutting system 6 describes the different roles served by the clamp 52. When the circular saw blade 38 is making a cut in the catheter 8, the clamp 52 holds the catheter 8 steady. When the cut has been made in the catheter 8, the catheter 8 is fed through the clamp 52 by causing the clamp to disengage from around the catheter 8. After being disengaged, the catheter 8 is fed through the clamp 52 until the next incision point on the catheter 8 is in position relative to the saw blade 38. The clamp 52 re-engages so as to be disposed snugly around the catheter 8 to again prevent movement of the catheter 8 during cutting.

It should be recognized from the description above that the width of a cut into the catheter 8 is limited to the width of the circular saw blade 38. A wider cut therefore requires that the catheter 8 be advanced slightly past the saw blade 38. However, advancement does not take place while making a cut. The saw blade 38 must be withdrawn so that the clamp 52 can disengage from around the catheter 8 while it is advanced. This is necessary because allowing cutting of the catheter 8 when the clamp is disengaged would create an imprecise or useless cut.

Figure 4A:
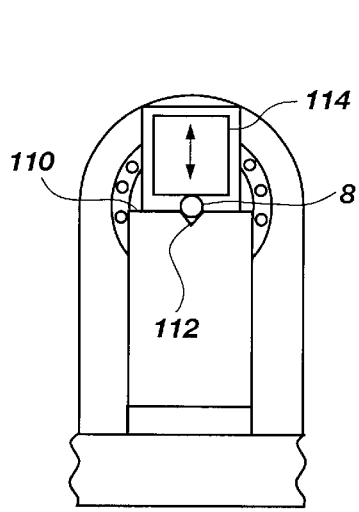
FIG. 4A is a front elevational view of an alternative embodiment for the clamping means.
Figure 4B:
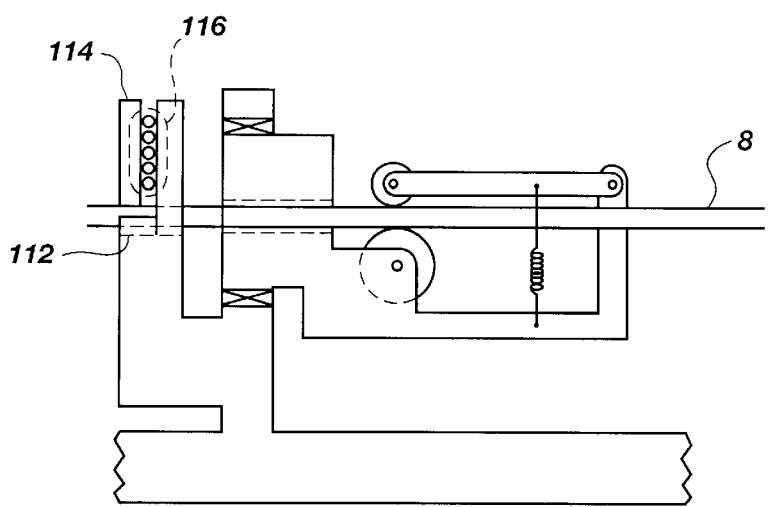
FIG. 4B is a side elevational view of the alternative embodiment for the clamping means of FIG. 4A.

Variations of the preferred embodiment are illustrated in FIGS. 4A and 4B which show that the clamping means 52 has been modified. As can be seen in FIG. 4A, a stationary support surface 110 is provided with a slot 112 therein for supporting the catheter 8 from below. The slot 112 guides and holds the catheter 8 before, during and after cutting. Holding the catheter 8 not only allows more precise cutting, but prevents damage to the catheter 8 which might otherwise occur. A movable clamping member 114 or anvil is also provided to thereby apply force to the catheter 8 which is clamped between the anvil 114 and the slotted support surface 110. FIG. 4B also shows that the anvil 114 has a mechanism 116 which allows the anvil 114 to move vertically with respect to the support surface 110. In FIG. 4B the vertical movement mechanism 116 is shown as bearings.

Figure 4C:
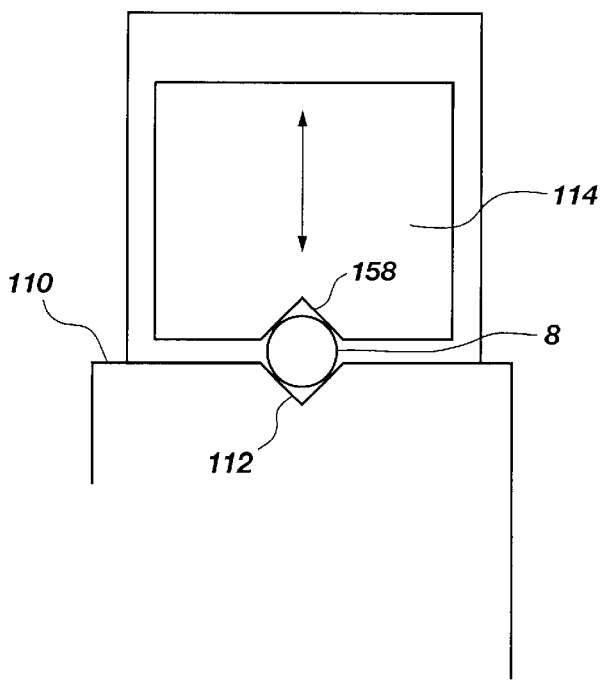
FIG. 4C is a front view which shows that the anvil has a slot.

FIG. 4C is provided to illustrate an alternative embodiment of the anvil 114. As shown, the anvil 114 has a slot 158 which will hold the catheter 8 more securely for cutting.

Figure 5:
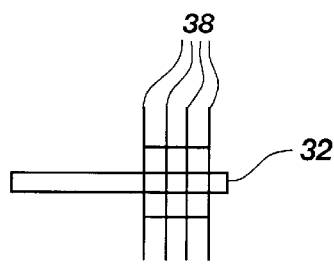
FIG. 5 is an alternative saw blade assembly which can be used in all embodiments of the present invention.

FIG. 5 illustrates a modification to the spindle 32 and saw blade 38 arrangement shown in FIGS. 1A and 1B. Specifically, a plurality of saw blades 38 are shown as being mounted in parallel on the same spindle 32. This also means that the saw blades 38 are necessarily coaxial. It is also preferred that the saw blades 38 have the same diameter so that no individual saw blade 38 makes a deeper incision in the catheter 8 than any of the others. However, it should be apparent that if the spindle 32 or the saw blades 38 are easily detachable from the system 6, then saw blades of varying diameters might be mounted on the same spindle 32 to achieve a consistent pattern of cuts having different depths.

Figure 6:
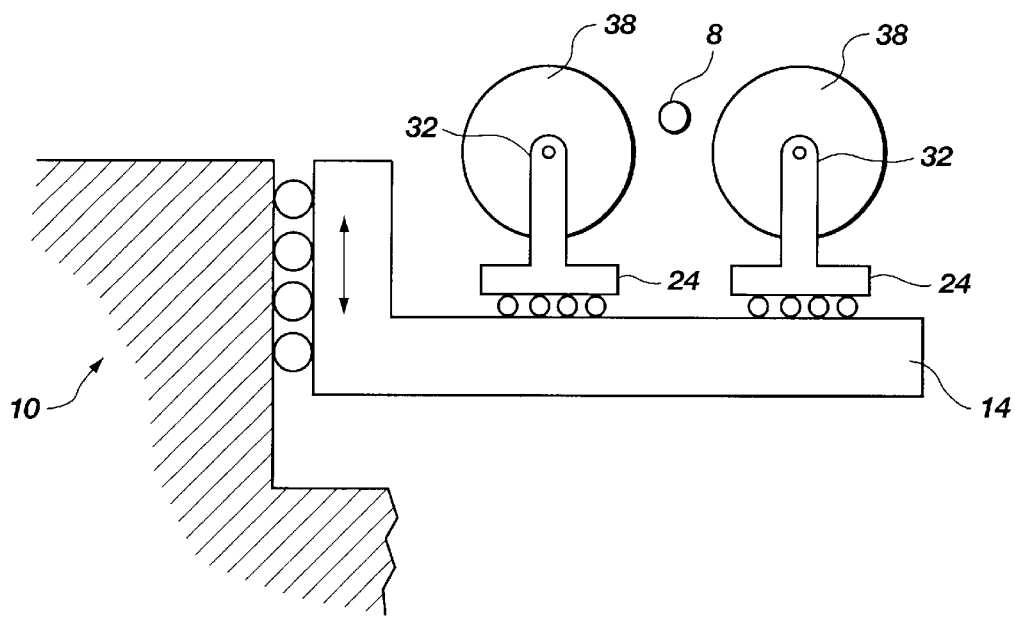
FIG. 6 is an alternative embodiment which uses two saw blade assemblies to simultaneously make incisions in the catheter.

FIG. 6 is an illustration of another alternative embodiment of the present invention. The vertically movable member 14 is shown having another shape which enables it to have disposed thereon two horizontally movable members 24, each having its own associated saw blade or blades 38. This embodiment enables the catheter 8 to be simultaneously cut at different circumferentially defined points on the catheter surface. This is especially useful in making multiple cuts in catheters, for example, on diametrically opposed positions on the catheter 8.

Figure 7:
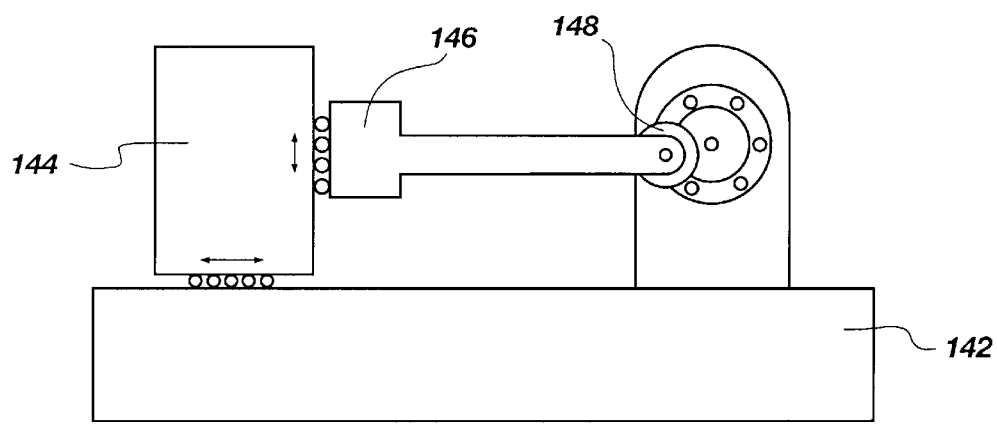
FIG. 7 is a side view of an alternative embodiment which shows a configuration with a base member, a horizontally movable member, and a vertically moveable member.

It should be noted that while the preferred embodiment has been defined as having a horizontally movable member with the spindle for the saw blade coupled thereto, the placement of the vertically and horizontally movable members can be switched as shown in FIG. 7. In this arrangement, the horizontally movable member 144 is coupled to the base member 142 and the vertically movable member 146, and the vertically movable member 146 has a spindle 148 rotatably coupled thereto.

Figure 8:
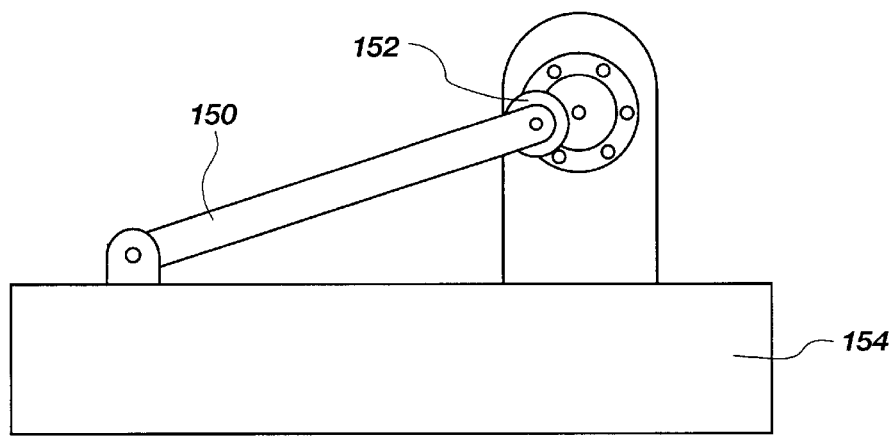
FIG. 8 is another side view of an alternative embodiment which shows a configuration of a base member, and a lever arm which moves the cutting blade in horizontal and vertical directions.

In another alternative embodiment of the present invention, shown in FIG. 8, a lever arm 150 is pivotally connected to the base member 154, and is capable of movement in at least two degrees of freedom so that it can move vertically and horizontally to position a spindle end 152.

Another aspect of the invention which should be clarified is that rotating the catheter is not limited to using a rotatable clamping mechanism. For example, the clamp can be non-rotatable and disengaged to enable the catheter feeding mechanism to rotate the catheter, and then re-engage the clamp to make additional incisions. Furthermore, the clamp and the catheter feeding mechanism can be rotated together before additional incisions are made.

Alternative aspects of the invention include the substitution of a non-mechanical cutting instrument for the rotating blade of the presently preferred embodiment. For example, a laser can be provided for cutting through materials which are mounted on the system.

It should also be realized that rotating blades are not the only type of mechanical blade which can be utilized. Conventional "sawing" blades can also be provided.

It is to be understood that the above-described embodiments are only illustrative of the application of the principles of the present invention. Numerous modifications and alternative arrangements may be devised by those skilled in the art without departing from the spirit and scope of the present invention. The appended claims are intended to cover such modifications and arrangements.

What is claimed is:

1. A system configured for forming at least one precision cut in an elongate object, wherein the precision cut is generally at an angle or transverse relative to a lengthwise axis of the elongate object, said system comprising:

a base; clamp supported by the base and configured for selectively grasping and stabilizing the elongate member by repeatedly releasing and then holding the elongate object in a position suitable for cutting;

a first roller and a second roller comprising a pinch roller and feed roller, the first and second rollers being rotatable supported by the base, and configured to move the elongate object in a direction parallel to the lengthwise axis, said rollers being rotatable with the elongate object around the lengthwise axis of the elongate member;

a mechanism configured for rotating the elongate object, said mechanism being supported by the base and configured to rotate the first and second roller; and, a horizontally moveable member supported by the base and configured for moving horizontally with respect to the base, a cutting means carried by the horizontally moveable member and moveable therewith toward and away from the elongate object, the cutting means being configured for forming the at least one precision cut in the elongate object to a desired depth.

2. A cutting system as defined in claim 1, further comprising a vertically moveable member disposed between the horizontally moveable member and the base, the horizontally moveable member being carried by the vertically moveable member, whereby the cutting means is moveable vertically and horizontally.

3. A cutting system as defined in claim 1, wherein the clamp further comprises a plurality of opposing surfaces which are movable to press against the elongate object and hold the elongate object immobile.

4. A cutting system as defined in claim 3 wherein the clamping device is further comprised of means for rotating the clamp is rotatable about the lengthwise axis of the elongate object.

5. A cutting system as defined in claim 3 wherein the comprises of a collet clamp.

6. A cutting system as defined in claim 1, wherein the cutting means is selected from the group of cutting means consisting of a mechanical blade and a laser.

7. The cutting system as defined in claim 6 wherein the mechanical blade is selected from the group of mechanical blades consisting of rotating saw blades and non-rotating saw blades.

8. A cutting system as defined in claim 1, wherein the clamp comprises a collet clamp.

9. A cutting system as defined in claim 1, wherein the clamp is rotatable with the mechanism configured for rotating the elongate, and wherein the clamp is rotatably carried by the base.

10. A cutting system as defined in claim 1, wherein the clamp and the pinch roller and feed roller are rotatably supported by the base and are configured to rotate together.

11. A cutting system as defined in claim 1, further comprising a crossed roller bearing slide, and wherein the horizontally movable member is carried by said slide.

12. A system configured for forming at least one precision cut in an elongate object, wherein the precision cut is generally at an angle or transverse relative to a lengthwise axis of the elongate object, said system comprising: a base;

a collet clamp configured for repeatedly releasing and then holding the elongate object in a position suitable for cutting the elongate object at an angle or transversely relative to the lengthwise axis;

a pinch roller assembly configured for manipulating the elongate object so that the elongate object can be moved to a position suitable for cutting when the object is released by the collet clamp, said pinch roller assembly comprising:

a first wheel configured for supporting and forcing the elongate object to move toward the clamping means when the collet clamp is disengaged;

a second wheel configured for applying a force to the elongate object to thereby hold the elongate object against the first wheel, thereby cooperating with the first wheel in providing friction to push the cylindrical object to the collet clamp; and a lever arm coupled to the base at a pivoting end, and coupled to the second wheel at a movable end;

a spring means coupled between the lever arm and the base and cooperating therewith to provide force to the second wheel for application to the elongate object; a mechanism configured for rotating the elongate object, said mechanism being supported by the base and configured to rotate said pinch roller assembly; and a movable member carrying a spindle configured to rotatable carry a rotatable blade configured for forming the at least one precision cut in the elongate object to any desired depth, said blade being moveable relative to the elongate object being held by the collet clamp such that the precision cut can be made at an angle or transversely relative to the lengthwise axis of the elongate object.

13. The system as defined in claim 12, wherein the clamp is rotatable about the lengthwise axis of the elongate object.

14. The system as defined in claim 12, wherein the blade is moveable toward and away from the elongate member in substantially horizontal directions.

15. The system as defined in claim 14, further comprising a vertically movable member configured to carry the movable member, wherein the blade is moveable toward and away from the elongate member in substantially vertical directions.

* * * * *

UNITED STATES PATENT AND TRADEMARK OFFICE
CERTIFICATE OF CORRECTION

PATENT NO.    : 6,260,458 B1
DATED         : July 17, 2001
INVENTOR(S)   : Jacobsen et al.

It is certified that error appears in the above-identified patent and that said Letters Patent is hereby corrected as shown below:

<u>Column 6,</u>
Line 66, insert the word -- a -- before the word "clamp"

<u>Column 7,</u>
Line 5, replace the word "rotatable" with the word -- rotatably --
Line 12, replace the word "roller" with the word -- rollers --
Line 33, replace the term "clamping device" with the word -- clamp --
Lines 33 and 34, eliminate the phrase "is further comprised of means for rotating the clamp"
Line 37, insert the word -- clamp -- before the word "comprises"
Line 37, eliminate the word "of" before the word "a"
Line 49, insert the word -- object -- after the word "elongate"

<u>Column 8,</u>
Line 35, replace the word "rotatable" with the word -- rotatably --

Signed and Sealed this

Eighth Day of June, 2004

JON W. DUDAS
*Acting Director of the United States Patent and Trademark Office*